United States Patent
DiGianfilippo et al.

(10) Patent No.: US 7,252,122 B2
(45) Date of Patent: *Aug. 7, 2007

(54) BULK COMPOUNDER MANIFOLD

(75) Inventors: Aleandro DiGianfilippo, Scottsdale, AZ (US); Kenneth C. Raines, Bethlehem, PA (US); Joel Bartholomew, Danielsville, PA (US); Richard S. Pierce, Glendale, AZ (US); Jeffery Steigerwalt, Lehighton, PA (US)

(73) Assignee: B. Braun Medical Inc., Allentown, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/285,239

(22) Filed: Nov. 22, 2005

(65) Prior Publication Data

US 2006/0070684 A1    Apr. 6, 2006

Related U.S. Application Data

(63) Continuation of application No. 11/048,154, filed on Feb. 2, 2005, now Pat. No. 7,036,537, which is a continuation of application No. 10/727,930, filed on Dec. 4, 2003, now Pat. No. 6,951,228.

(51) Int. Cl.
*B65B 1/04* (2006.01)
*B67C 3/02* (2006.01)

(52) U.S. Cl. ............... 141/105; 141/104; 141/285; 141/302

(58) Field of Classification Search .......... 141/10, 141/100, 104, 105, 285, 286, 301, 302, 313; 137/512.4, 605, 606; 604/83, 247
See application file for complete search history.

(56) References Cited

U.S. PATENT DOCUMENTS

| 4,467,844 A | 8/1984 | DiGianfilippo et al. |
| 4,513,796 A | 4/1985 | Miller et al. |
| 4,648,430 A | 3/1987 | DiGianfilippo et al. |
| 4,653,010 A | 3/1987 | Figler et al. |
| 4,712,590 A | 12/1987 | Gianfilippo |
| 4,718,467 A | 1/1988 | DiGianfilippo et al. |
| 4,789,014 A | 12/1988 | DiGianfilippo et al. |
| 4,823,833 A | 4/1989 | Hogan et al. |
| 4,915,688 A * | 4/1990 | Bischof et al. ............... 604/83 |
| 4,922,975 A | 5/1990 | Polaschegg |
| 4,967,811 A | 11/1990 | DiGianfilippo et al. |

(Continued)

FOREIGN PATENT DOCUMENTS

WO    WO 03/058507 A1    7/2003

*Primary Examiner*—Khoa D. Huynh
(74) *Attorney, Agent, or Firm*—RatnerPrestia

(57) ABSTRACT

The present invention provides a manifold for receiving fluid tubes in a bulk compounder. In its simplest form, the manifold includes a plurality of inlets, each inlet defining an opening to a respective fluid passageway, and each passageway contains a check-valve. Included in this manifold is an outlet in fluid communication with the fluid passageways and an inlet port which is coaxial with the outlet. The coaxial inlet port contains a check-valve. Included as a part of the present invention is a cannula adapted for use with the manifold of the present invention, tube sets for use with the manifold of the present invention, and a method of minimizing error in filling a bag using a manifold in accordance with the present invention.

14 Claims, 13 Drawing Sheets

U.S. PATENT DOCUMENTS

| | | |
|---|---|---|
| 5,025,954 A | 6/1991 | Dunnous |
| 5,040,699 A | 8/1991 | Gangemi |
| 5,056,568 A | 10/1991 | DiGianfilippo et al. |
| 5,076,332 A | 12/1991 | Lewis et al. |
| 5,085,256 A | 2/1992 | Kircher et al. |
| 5,313,992 A | 5/1994 | Grabenkort |
| 5,316,181 A | 5/1994 | Burch |
| 5,364,526 A | 11/1994 | Matkovich et al. |
| 5,402,834 A | 4/1995 | Levin et al. |
| 5,431,185 A | 7/1995 | Shannon et al. |
| 5,431,201 A | 7/1995 | Torchia et al. |
| 5,431,202 A | 7/1995 | Dikeman et al. |
| 5,450,847 A | 9/1995 | Kampfe et al. |
| 5,464,047 A | 11/1995 | Muscara |
| 5,470,488 A | 11/1995 | Matkovich et al. |
| 5,507,412 A | 4/1996 | Ebert et al. |
| 5,510,621 A | 4/1996 | Goldman |
| 5,511,594 A | 4/1996 | Brennan et al. |
| 5,592,940 A | 1/1997 | Kampfe et al. |
| 5,597,094 A | 1/1997 | Vilbert |
| 5,626,172 A | 5/1997 | Schumacher et al. |
| 5,637,103 A | 6/1997 | Kerwin et al. |
| 5,697,407 A | 12/1997 | Lasonde |
| 5,750,998 A | 5/1998 | Goldman |
| 5,772,966 A | 6/1998 | Maracas et al. |
| 5,820,048 A | 10/1998 | Shereyk et al. |
| 5,836,923 A | 11/1998 | Mayer |
| 5,927,349 A | 7/1999 | Martucci et al. |
| 6,079,462 A | 6/2000 | Martucci et al. |
| 6,199,603 B1 | 3/2001 | DiGianfilippo et al. |
| 6,202,711 B1 | 3/2001 | Martucci et al. |
| 6,213,174 B1 | 4/2001 | Cook et al. |
| 6,296,450 B1 | 10/2001 | Westberg et al. |
| 6,319,243 B1 | 11/2001 | Becker et al. |
| 6,669,681 B2 | 12/2003 | Dudar et al. |
| 7,036,537 B2 * | 5/2006 | DiGianfilippo et al. ..... 141/105 |
| 2002/0035412 A1 | 3/2002 | Kircher et al. |

* cited by examiner

BULK COMPOUNDER MANIFOLD

CROSS REFERENCE TO RELATED APPLICATIONS

This application is a continuation of U.S. patent application Ser. No. 11/048,154 filed Feb. 2, 2005 now U.S. Pat. No 7,036,537, which is a continuation of U.S. patent application Ser. No. 10/727,930, filed Dec. 4, 2003 now U.S. Pat. No. 6,951,228.

FIELD OF THE INVENTION

The present invention relates to bulk nutritional compounders and more specifically to manifolds for use in bulk nutritional compounders.

BACKGROUND OF THE INVENTION

Hyperalimentation therapy is the intravenous feeding of nutrients to patients. A typical solution would include a protein-carbohydrate mixture. It is used primarily to meet the patient's protein and caloric requirements which are unable to be satisfied by oral feeding. The protein may be in the form of free-amino acids or protein hydrolysate and the carbohydrate commonly is dextrose. In addition to the protein and carbohydrate, vitamins (water-soluble and fat-soluble) and electrolytes also can be supplied in this therapy.

Each of these parenteral ingredients and the combination thereof are particularly susceptible to the growth of deleterious organisms and it is desirable that they be administered to the patient in a sterile condition. In addition, the solutions are tailor made to specific patient requirements under the direction of a physician. Thus, because these protein and carbohydrate solutions must be combined close to their time of use, their compounding must be performed under sterile conditions to avoid organism growth.

As a part of this compounding, the solutions that are to be administered intravenously are transferred into a total parental nutrition bag (commonly referred to as a TPN bag). Such bags are designed for home use or use in a hospital or care facility. Once filled they can be stored for a limited period of time in a standard refrigerator. The bags are filled with the solutions by a pharmacist either by gravity or by a device known as a high speed bulk compounder. Such compounders typically are capable of supplying solutions from up to nine different source bags or containers to a receiving product bag at relatively high flow rates.

The source containers may be hung from a framework of the compounder while the receiving bag is hung from a load cell that measures the weight of the receiving bag. A pump set consisting of a number of pump legs (for example, nine or more such legs) or flow paths is designed to be used with the compounder. Each of the pump legs includes flexible tubing and terminates on one end with a piercing administration spike or similar connector that is used to connect the leg of the pump set to one of the source containers. The other end of each leg is coupled to one of the inlet ports of a common manifold equipped with an exit port that is adapted to be coupled to a fill tubing connected to the receiving TPN product bag.

In those instances where a high-speed compounder is used, each leg of the pump set is associated with a different peristaltic pump or pump station of the compounder. A microprocessor in the compounder controls each of the peristaltic pumps or pump stations to thereby control the amount of solution being supplied from each source container through the particular pump leg and the manifold to the receiving product bag. The amount of solution being supplied from each source container is in part determined by information being supplied to the microprocessor of the weight being measured at selected times by the load cell from which the receiving bag is suspended. The peristaltic pumps draw solutions from each of the source containers sequentially under the control of the microprocessor and the solutions flow through the common manifold and the fill tubing into the receiving product bag.

A typical compounder would have several source bags and affiliated tubes. Typically, there are six or nine pumping stations for six or nine different source solutions. The microprocessor in the compounder is programmed to sequentially fill the product bag with each ingredient, one at a time, by sequentially activating each of the six pump stations individually so that the solutions from each source bag are transferred via the common manifold and the fill tubing to the product bag. Then, after the product bag is supplied with the required amount of fluids, the fill tubing from the product bag is sealed.

Because all tubes in such a configuration flow into a common manifold, but only one fluid at a time is pumped through the common manifold, it is possible that some fluid from a particular source bag flows back through the common manifold and into a feed tube from another source bag containing a different fluid. The fluid that does flow back into a different feed tube is not weighed as a part of the product bag and the compounder microprocessor does not recognize that fluid as a part of the overall make-up of the product bag. The problem with this is that once the product bag receives the weight of a particular ingredient, the microprocessor shuts off that respective pump and turns to the next source bag. The microprocessor begins pumping the fluid from that second source bag into the product bag but in so doing causes the backed-up and stored fluid from the first product bag in that supply tube to now flow into the manifold and ultimately into the product bag. At that point, however, the weight gain in the product bag is recognized by the compounder microprocessor as being due to the second fluid. This error leads to the situation where too much of the first fluid is present in the product bag and not enough of the second fluid is present in the bag.

A related problem arises when one of the fluids to be introduced into the product bag is a lipid solution. Lipid solutions are essentially fat emulsions and typically are placed into a separate compartment within the product bag which is isolated from the remaining mixture until immediately before (or very soon before) the solution is administered to a patient. This isolation is necessary because the lipid solution, if mixed with the other ingredients ahead of time, clouds the overall solution mixture and renders it unusable. This phenomena is known in the art as "hazing." Because of the undesirability of mixing lipids with the other solutions prior to the time of administration, a problem has existed in the prior art where a residual amount of the lipid solution is allowed to remain in a common volume of the manifold after a lipid solution is pumped through but before the next non-lipid solution is pumped through. When the subsequent solution is pumped through, the residual lipid solution is carried into the product bag and hazing results.

SUMMARY OF THE INVENTION

The present invention provides a manifold for receiving fluid tubes in a bulk compounder. In its simplest form, the manifold comprises a plurality of inlets, each inlet defining an opening to a respective fluid passageway, and each passageway contains a check-valve. Included in this manifold is an outlet in fluid communication with the fluid passageways, and an inlet port which is coaxial with the outlet. The coaxial inlet port preferably contains a check-valve.

Also included as a part of the present invention is a manifold set for receiving fluid tubes in a bulk compounder. The manifold set comprises a manifold and a cannula. The manifold comprises a plurality of inlets, each inlet defining an opening to a respective fluid passageway, each passageway containing a check-valve, an outlet in fluid communication with the fluid passageways; and an inlet port which is coaxial with the outlet, the coaxial inlet port also containing a check-valve. The cannula has at least one male blunt tip for insertion into the self-sealing membrane, and preferably includes a female port disposed within the male blunt tip.

In a preferred embodiment of the present invention, a manifold for receiving fluid tubes in a bulk compounder is provided having a plurality of inlets, each inlet defining an opening to a respective fluid passageway, with each passageway containing a check-valve. The plurality of inlets are disposed radially around a center inlet, and an outlet is provided in fluid communication with all of the fluid passageways and center inlet. The outlet and the center inlet have the same central axis.

Also included as a part of the present invention is a tube set for use in bulk compounding. The tube set comprises a plurality of pump sections, each pump section having a distal end. Also included is a plurality of tubes, each tube of the plurality having a distal end and a proximal end, with each proximal end of each tube of the plurality attached to the distal end of a respective pump section. Additionally, each distal end of each tube of the plurality is attached to a manifold, wherein the manifold comprises a plurality of inlets, each inlet defining an opening to a respective fluid passageway, each passageway containing a check-valve. The manifold includes an outlet in fluid communication with the fluid passageways.

A preferred tube set in accordance with the invention comprises a plurality of pump sections, each pump section having a distal end and a proximal end, a first plurality of tubes, each tube of the first plurality attached to the proximal end of a respective pump section, and a second plurality of tubes, each tube of the second plurality having a distal end and a proximal end, with each proximal end of each tube of the second plurality attached to the distal end of a respective pump section. The distal end of each tube of the second plurality is attached to a manifold. The manifold comprises a plurality of inlets, each inlet defining an opening to a respective fluid passageway, each passageway containing a check-valve, and an outlet in fluid communication with the fluid passageways.

Also included in the present invention is a method of minimizing error in the filling of a product bag in a bulk compounding system. The method comprises the steps of providing a manifold with a minimum common volume to minimize residual holding of any one ingredient solution, and passing individual ingredient solutions through the manifold to fill a product bag. Error is reduced because of the minimization of the manifold common volume step.

Still also included as a part of the present invention is a cannula for attaching two fluid channels. The cannula comprises at least one male blunt tip end for insertion into a first fluid source, and a female port formed within the male blunt tip end to allow connection of the cannula to a different fluid source wherein the different fluid source has a male end.

BRIEF DESCRIPTION OF THE DRAWINGS

The invention is best understood from the following detailed description when read in connection with the accompanying drawings, in which:

FIG. 3b shows an exploded view of the main body portion shown in FIG. 3a;

FIG. 5b shows an exploded view of the valve housing shown in FIG. 5a;

FIG. 10b is a view of the assembled device shown in FIG. 10a.

DETAILED DESCRIPTION OF THE INVENTION

The present invention provides a manifold having a one-way valve, or check valve, disposed within each inlet of the manifold. Additionally, the manifold has a plurality of inlets, with at least one inlet disposed proximate to, and coaxially with, an outlet. The purpose of the coaxially disposed inlet/outlet is to minimize the volume through which the solution passed into the coaxial inlet must travel, thereby lowering the amount of potential residue that can be left behind by that particular solution. In a preferred embodiment, this line is used to transport a lipid solution. Other aspects of the manifold according to the present invention which will be described in more detail below also contribute to the reduction in common volume thereby reducing error in the final product bag composition due to residue buildup within the manifold.

Figure 1:
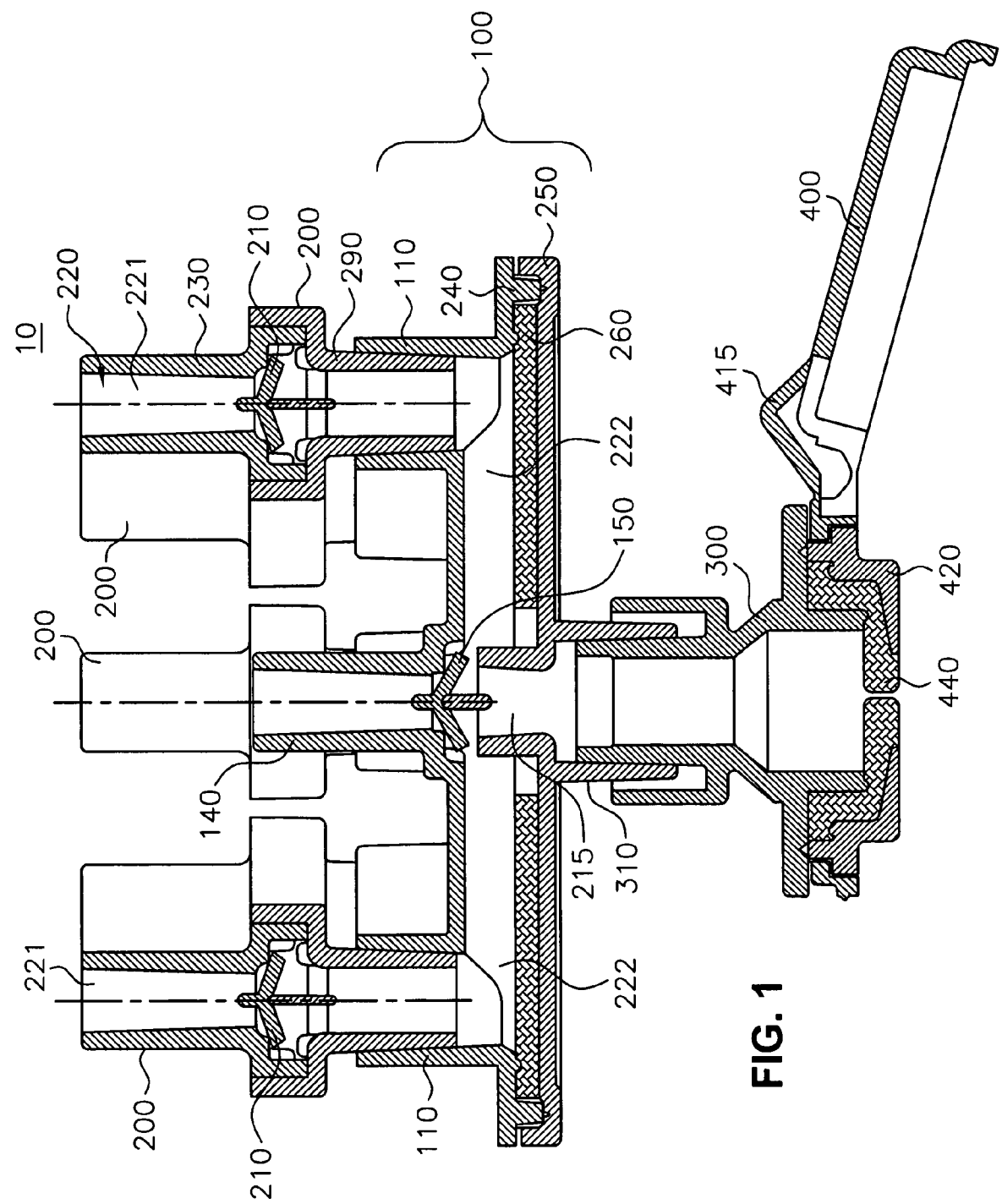
FIG. 1 is a partial cross-sectional view of a device according to the present invention, including a manifold body portion, valve housings, and an outlet tube connector.

FIG. 1 shows a partial cross-sectional view of a manifold 10 in accordance with one embodiment of the present invention. In this embodiment, manifold 10 has a main body portion 100, a plurality of valve housings 200, and an outlet tube connecter 300. Specifically, each of a plurality of inlets 220 leads to a respective fluid passageway 221, in which is disposed a check-valve disk 210. As used herein, the terms, "check-valve" and "one-way valve" are intended to be synonymous. Fluid passed across each check-valve disk 210 flows along its respective flow path through flow channels 222 in main body portion 100 and into a common central chamber 215 which is in fluid communication with each respective flow channel 222 and, subsequently, each fluid passageway 221. Common central chamber 215 fluidly connects all of the flow channels 222 and center port 140 (discussed in more detail below) to manifold outlet port 310 and ultimately to manifold outlet tube connector 300.

In the case of a preferred embodiment, each of the three main components (main body portion 100, a plurality of valve housings 200, and an outlet tube connecter 300) can be fabricated independently and joined together to form a single device made up of its individual components. Preferably, each of these three main components is ultrasonically welded to its respective mate. The means of joining the components are discussed in detail below. The primary advantage to such a construction is ease of manufacture.

The manifold could be made from any of a number of suitable materials, including plastics, such as polycarbonates, that are suitable to handle the pharmaceutical and food preparations that will be passing therethrough. The suitable materials should also preferably be such that they can be injection molded to form the parts of the device, or the whole device, and one skilled in the art would know such materials.

More specifically, FIG. 1 shows valve housings 200 which are connected to their respective manifold main body portion openings 110. In a preferred embodiment, the valve housings 200 are connected to their respective manifold main body portion openings 110 by ultrasonic welding. Ultrasonic welding is a technique known to those skilled in the art for fastening plastic to plastic. Additional means of connection could be employed, however, including solvent welding, adhesives, snap-fittings, flanges, or any other suitable connection known to one skilled in the art.

Figure 2:
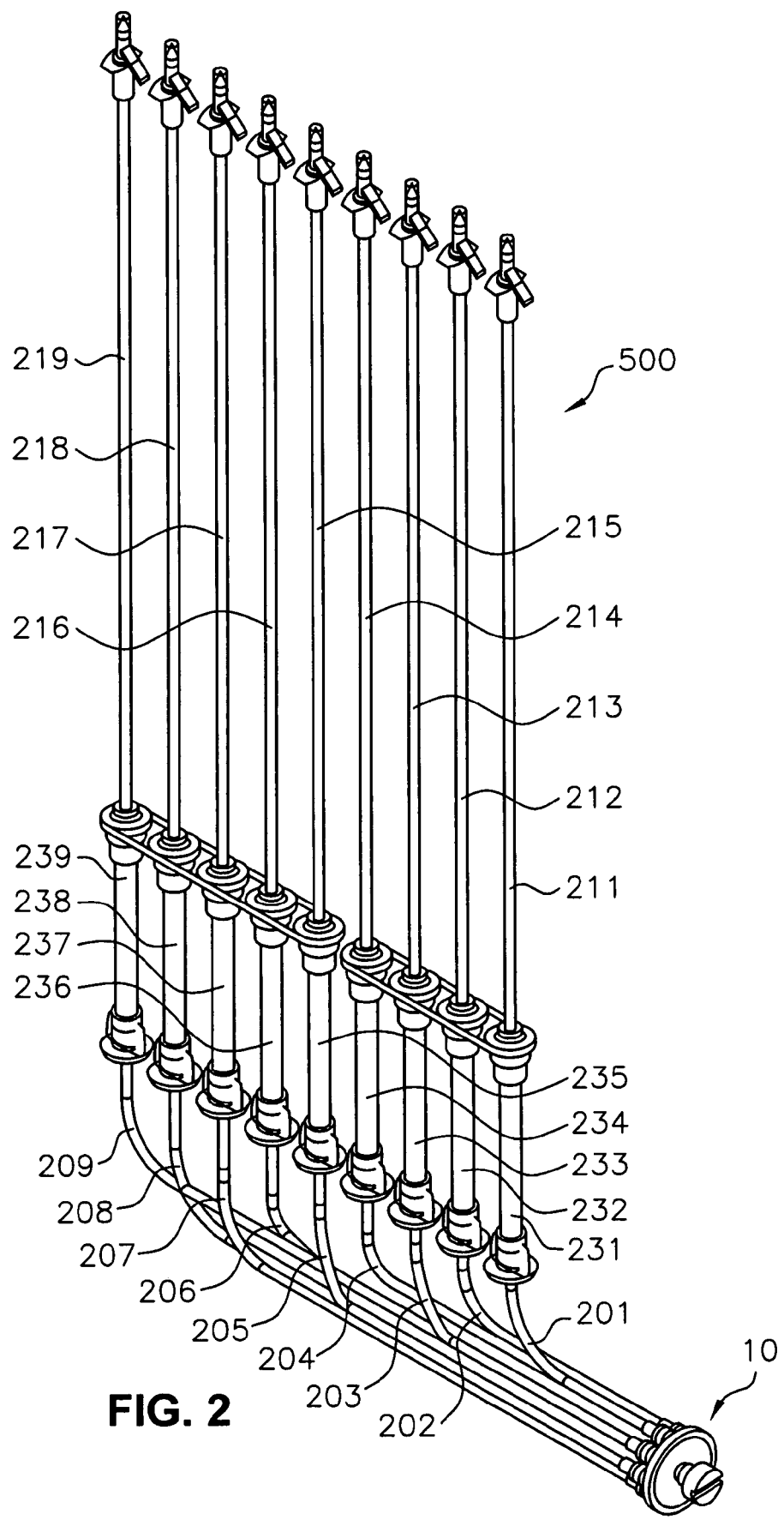
FIG. 2 illustrates a tube set in accordance with the present invention using the manifold of FIG. 1.

FIG. 2 shows a manifold 10 in accordance with the present invention disposed at the end of a tube set 500. In this particular embodiment, manifold 10 has nine inlets, one for each feed tube 201-209. In this configuration, feed tubes 201-209 carrying respective fluids, such as from a pump disposed between the manifold 10 and respective fluid source bags (not shown), are connected to the top openings 220 of valve housings 200. Preferably, feed tubes 201-209 are connected to manifold 10 by having each of their distal ends placed over its respective top opening 220 of each respective valve housing 200. These tubes would be attached via friction fit or other means known to those skilled in the art, including with the use of adhesives. FIG. 2 also shows upper tubes 211-219, each of which extends from a respective source bag (not shown) as noted above. Pump sections 231-239 are shown connecting the proximal ends of feed tubes 201-209 to the distal ends of upper tubes 211-219. These pump sections are where the pump (not shown) operates on the tube set.

FIG. 2 also shows tubing organizer 291 attached to the macro compounder transfer set. Tubing organizer 291 is preferably a semi-flexible plastic member that aligns the tubing pump segments (e.g. 6 or 9) for easy insertion into the compounder. The organizer includes an offset rail that acts as a key to insure that the pump segments are loaded in proper sequence left to right. The organizer also acts as a packaging aid to prevent tangling of the set inside the finished package.

FIG. 1 also shows a center port 140 which is coaxial with outlet tube connector 300. Preferably, and as shown in FIG. 1, check-valve disk 150 (a one-way valve) is disposed within center port 140. The details of suitable check-valves are discussed in more detail below, but generally are known to those skilled in the art. The fact that center port 140 is proximate to, and coaxial with, manifold outlet port 310 and, ultimately, manifold outlet tube connector 300, is important where center port 140 is intended to be used as a means to deliver a lipid solution to the product bag. As discussed above, the presence of lipid residue within the manifold is deleterious. Thus, by minimizing either or both of the common volume within the manifold where any such lipid solution could accumulate, and the flow volume within the manifold for the lipid fluid itself, one achieves a concomitant reduction in the amount of any residue of lipids that could later be passed to the wrong part of the product bag. This is one advantage realized by the present invention's placement of the lipid port, or opening, in line with the exit port. Such a configuration achieves the smallest possible volume through which the lipid solution needs to pass within the manifold, thereby minimizing any lipid residue.

Figure 3A:
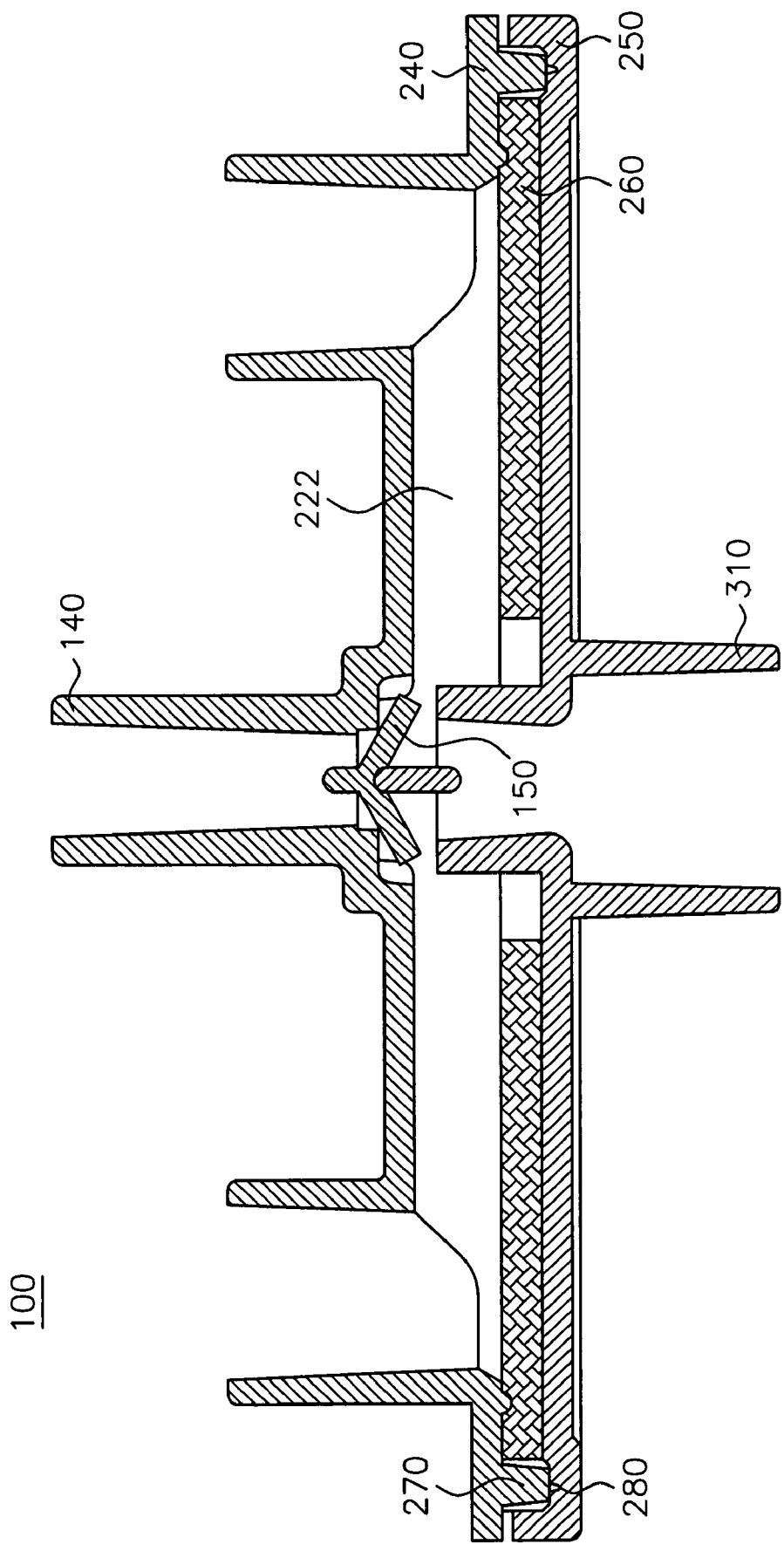
FIG. 3a shows a cross-sectional view of the main body portion of the manifold of FIG. 1 without valve housings or the outlet tube connector shown in FIG. 1.

FIG. 3a shows a view of manifold body portion 100 without valve housings 200 or outlet tube connector 300. In this particular embodiment, manifold main body portion 100, as discussed above, has a center port 140 which is coaxial with manifold outlet port 310 and has check-valve disk 150 disposed within it. As shown in the drawings, manifold main body portion 100 is comprised of manifold top 240, manifold bottom 250, and manifold gasket 260 disposed therebetween. A preferable material of construction for the gasket is silicone. In the embodiment shown in FIG. 3a, center port 140 is formed as a part of manifold top 240, and manifold outlet port 310 is formed as a part of manifold bottom 250.

As noted above, FIG. 3a shows gasket 260 which fluidly seals top 240 to bottom 250 and along with flow channels 222 formed in top 240 forms respective fluid passageways as discussed in more detail below. Top 240 and bottom 250 can be attached in any number of ways known to those skilled in the art, including by ultrasonic welding. In order to aid in ultrasonic welding, male protrusion 270 extending from top 240 into female portion 280 formed in bottom 250 can be molded into the respective halves.

Figure 3B:
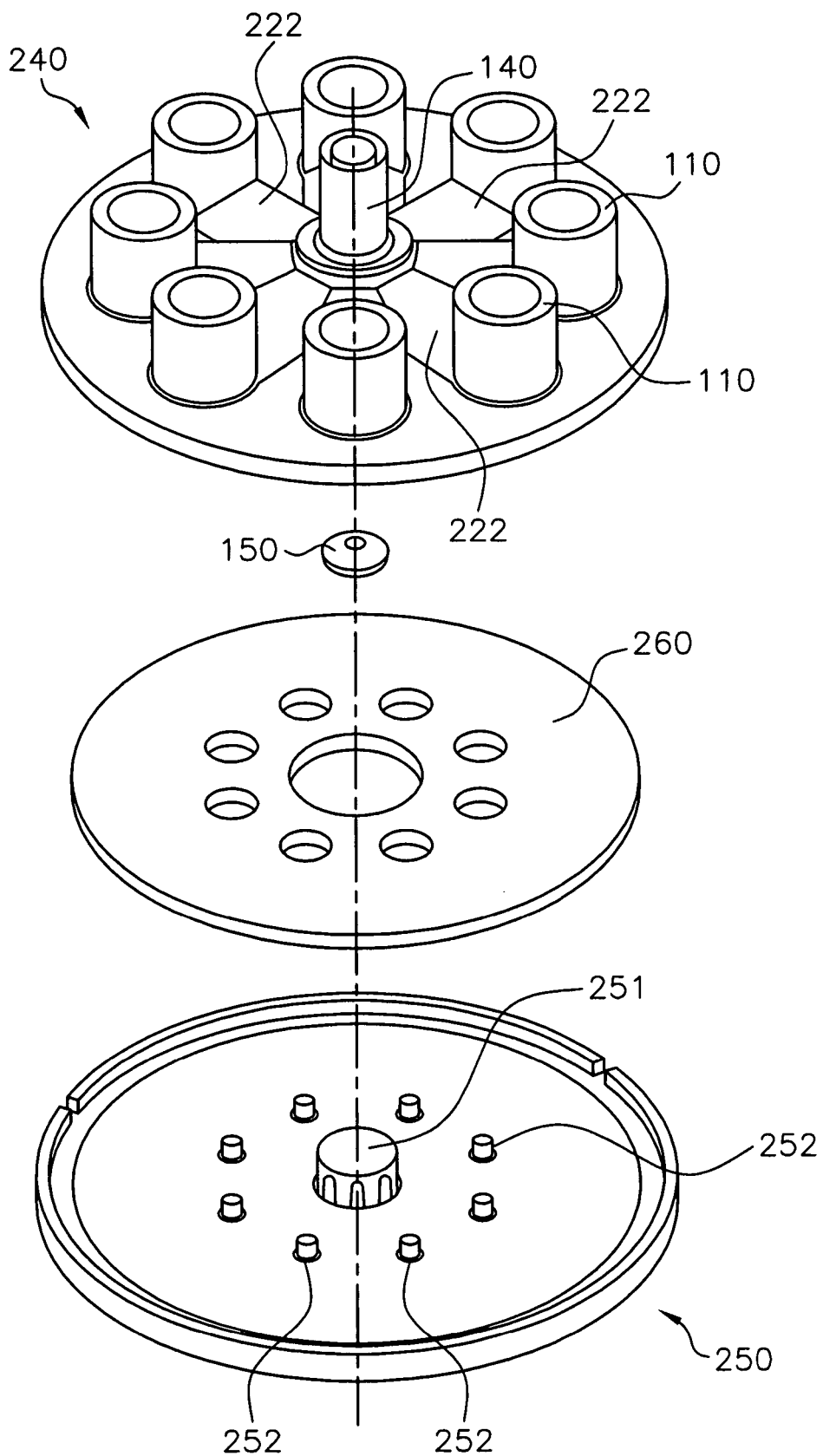
Figure 3C:
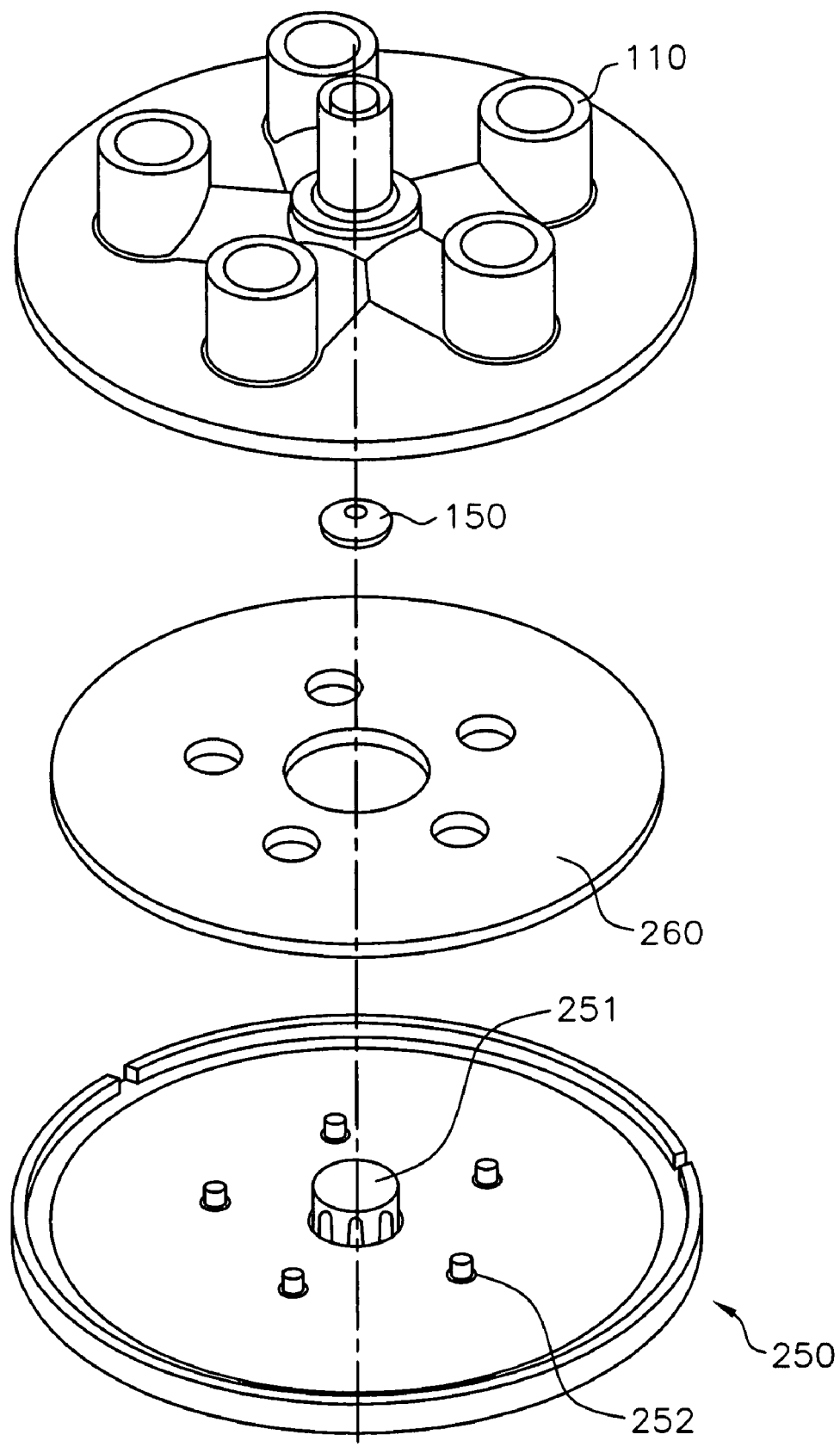
FIG. 3c shows an exploded view like that of FIG. 3b but with only six total inlet ports.

FIG. 3b shows an exploded view of the components discussed above with respect to FIG. 3a. Specifically, top 240 is shown with nine inlet ports, including eight radially disposed inlets 110 and center port 140. Also, eight flow channels 222 are shown formed in top 240. Check-valve disk 150 is a silicone disk disposed atop a mounting point 251 formed on bottom 250. As noted above, to aid in ultrasonic welding, protrusions may be formed on any suitable part. Shown in FIG. 3b are protrusions 252 formed on bottom 250. FIG. 3c shows a similar view as that which is shown in FIG. 3b but illustrates an embodiment having a total of only six ports.

Figure 4:
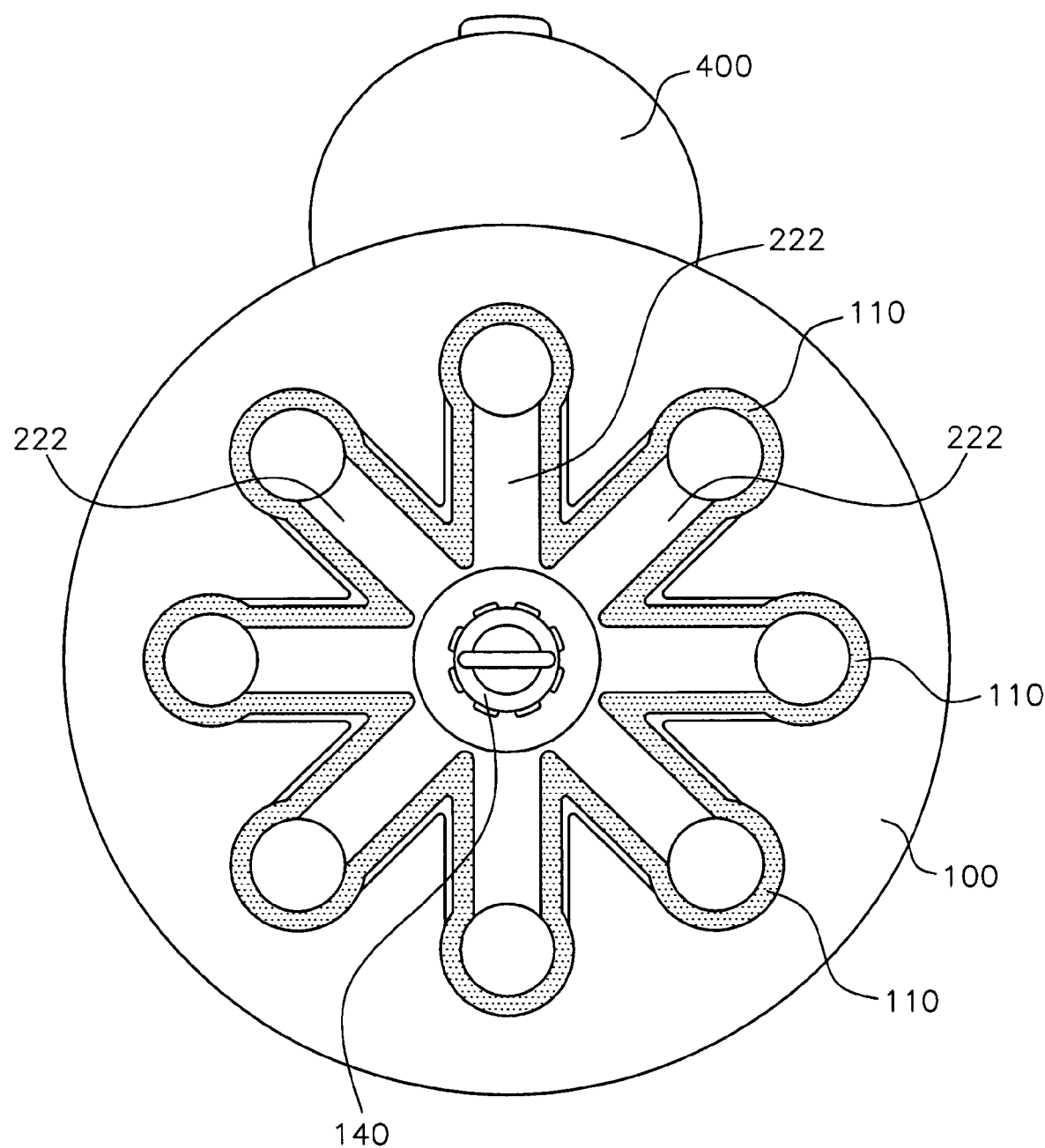
FIG. 4 shows a top view of the manifold shown in FIG. 1.

FIG. 4 shows a view of the manifold as shown in FIG. 3b but from the top (or proximal) side of the manifold having manifold openings 110 disposed radially outward from center port 140. As discussed above, fluid flow channels 222 are formed in manifold top 240 which, along with gasket 260, form individual flow channels connecting each inlet fluid passageway 221 with common central chamber 215. The manifold should be capable of delivering fluid at the rate of approximately one liter in 60 seconds. It is also preferable that the residual or common volume inside the manifold be less than two milliliters, with the smaller the common volume the better.

As can be seen in FIGS. 3b, 3c, and 4, each fluid passageway (with the exception of center port 140) is configured in a radial pattern with its own respective radial flow path and flow channel 222, each of which leads to common central chamber 215. Such a configuration, along with the presence of gasket 260, helps further an important part of the invention as discussed above, namely the minimizing of any common volume within the manifold. By providing these individual flow paths from each manifold opening 110 all the way to common central chamber 215, only common central chamber 215 of the manifold sees fluid from all source bags, instead of the entire space between manifold top 240 and manifold bottom 250 (such as would be the case without gasket 260). This minimum volume is further aided by the fluid passageways preferably having a semi-circular cross-section that results in high flow rates.

Figure 5A:
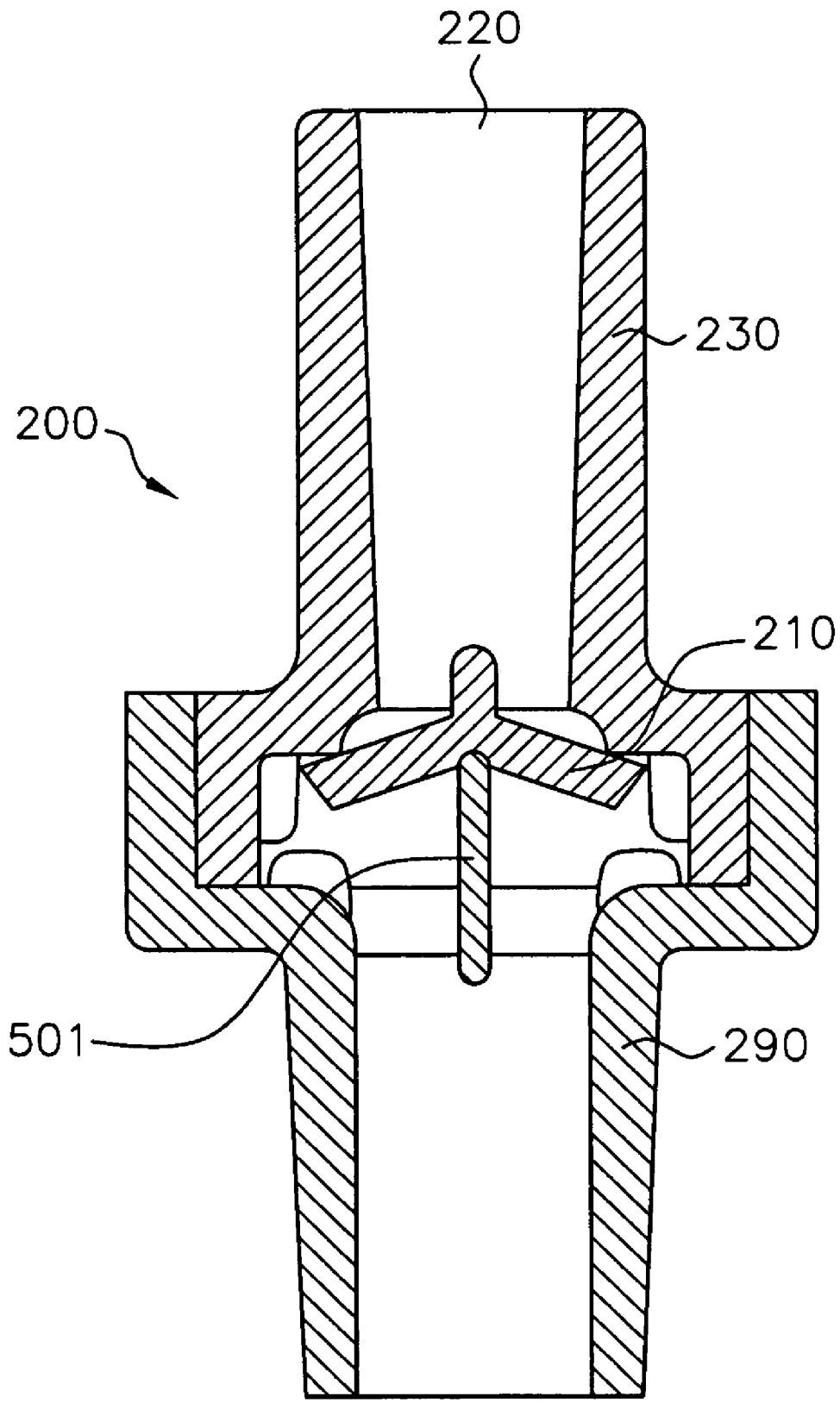
FIG. 5a shows a cross-sectional view of a valve housing in accordance with the present invention.
Figure 5B:
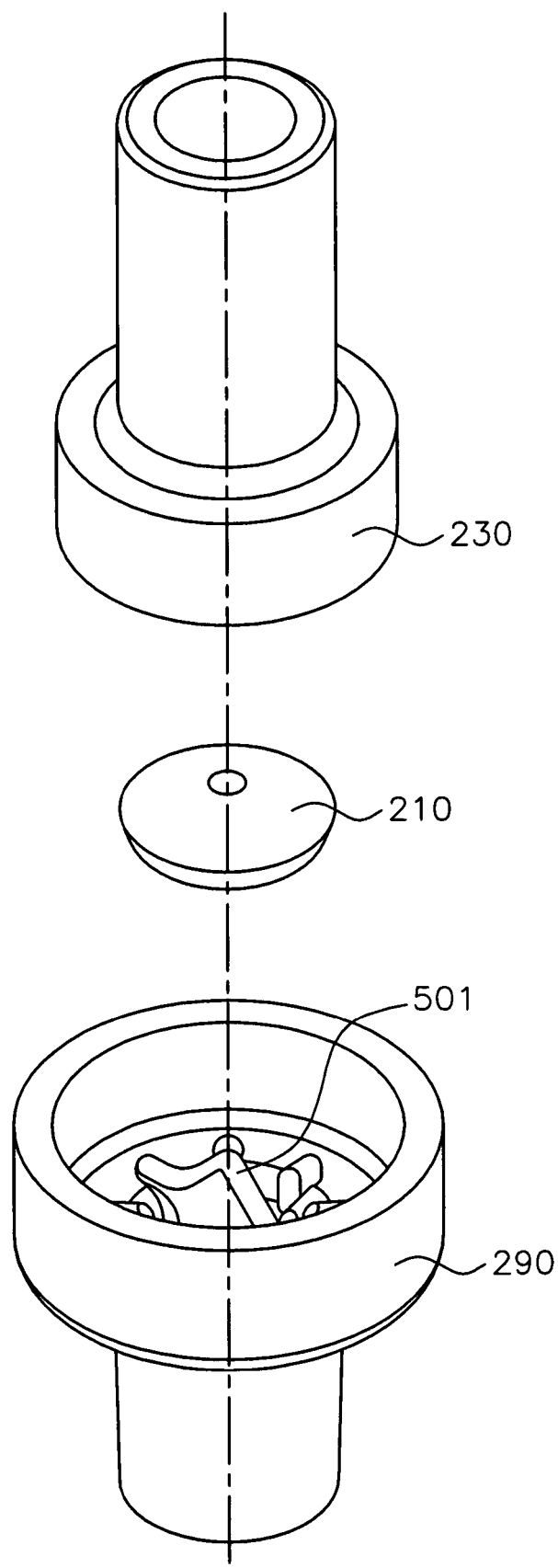

FIG. 5a shows a cross-sectional view of a single valve housing 200. As discussed above with respect to FIG. 1, valve housing 200 can be constructed as a single piece (not shown) or in pieces and then assembled to form a modular device. As shown in the drawings, a preferred valve housing 200 is modular and is comprised of valve upper half 230 and valve lower half 290. In this preferred embodiment, valve upper half 230 is solvent welded to valve lower half 290, and check-valve disk 210 is disposed therebetween atop a valve seat, namely mounting point 501. Solvent welding is known to those skilled in the art. A preferred solvent is methylene chloride, or a mixture of methylene chloride and tetrahydrofuran. Other means of connecting the valve halves would be known to those skilled in the art, however, and would include adhesives or ultrasonic welding. Moreover, the one-way valves as disclosed herein could take any of a number of forms known to those skilled in the art. Preferably, they would comprise a check-valve disk, preferably made from a silicone elastomer, disposed on a polycarbonate valve seat. FIG. 5b shows an exploded view of valve housing 200. Shown in FIG. 5b are valve upper half 230, check-valve disk 210, and valve lower half 290 containing mounting point 501.

Figure 6:
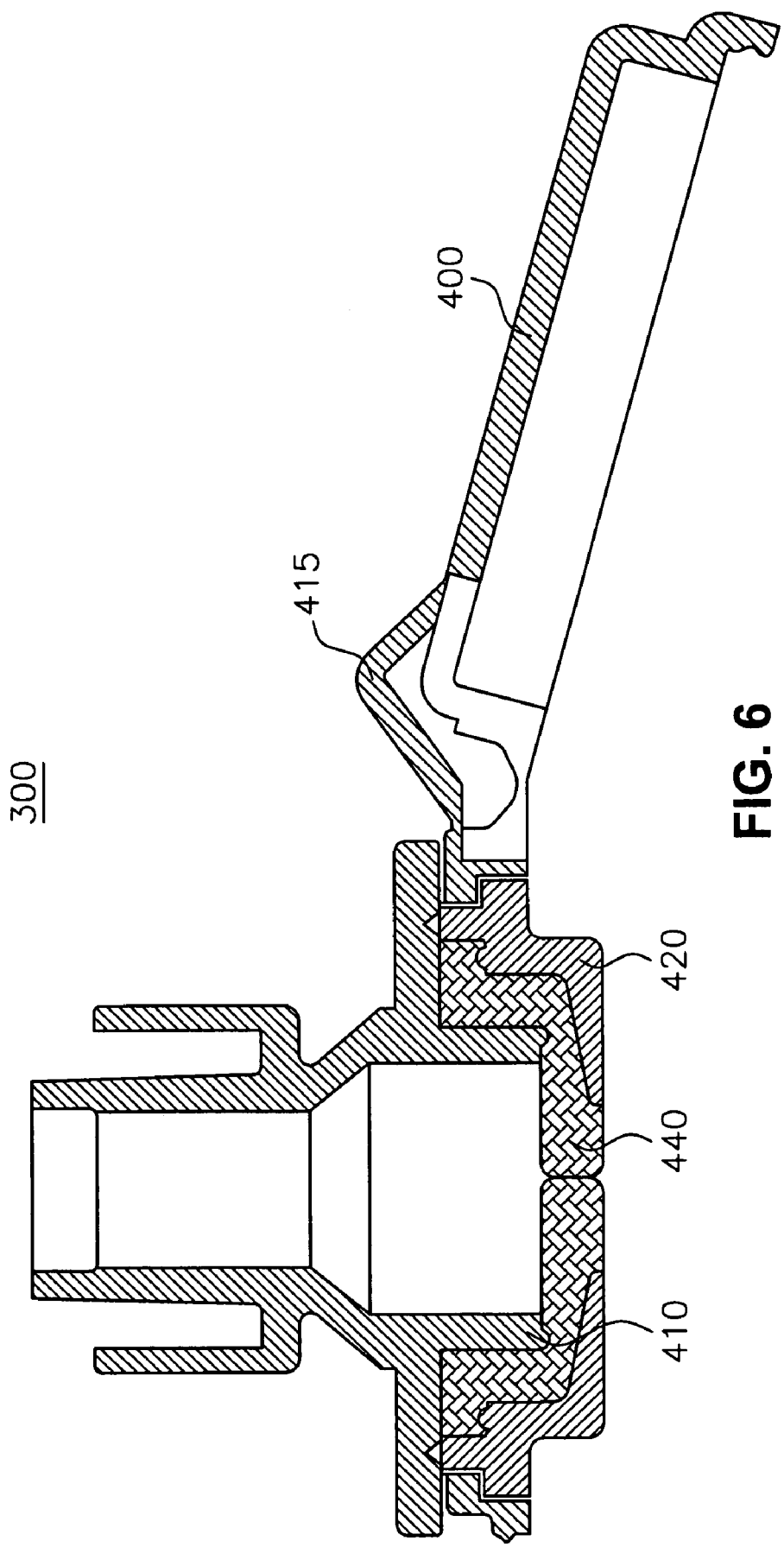
FIG. 6 is a cross-sectional view of an outlet tube connector in accordance with the present invention.

FIG. 6 shows a cross-sectional view of an exemplary outlet tube connector 300 by itself. As noted above with respect to FIG. 1, outlet tube connector 300 is preferably ultrasonically welded to manifold outlet port 310, although other means of connection would be known to those skilled in the art. FIG. 6 shows outlet tube connector including connector cap 400 which is attached to the distal end 410 of outlet tube connector 300 (the distal end being defined as the end furthest from manifold body portion 100). Connector cap 400 is attached via hinge 415 which is, in this embodiment, integrally formed with connector cap 400 and connector retention ring 420 which extends around distal end 410 of outlet tube connector 300.

Disposed between retention ring 420 and distal end 410 of outlet tube connector 300 is connector septum 440. This is generally a self-sealing membrane designed to close the opening when an outlet line is not connected to outlet tube connector 300. When a product bag is ready to be filled, a fill line to the product bag, typically having a spiked cannula (connector) or blunt cannula, is thrust or pushed into septum 440 to create a fluid communication between the fill line and manifold outlet tube connector 300. Self-sealing membranes of this type are known to those skilled in the art.

Figure 7:
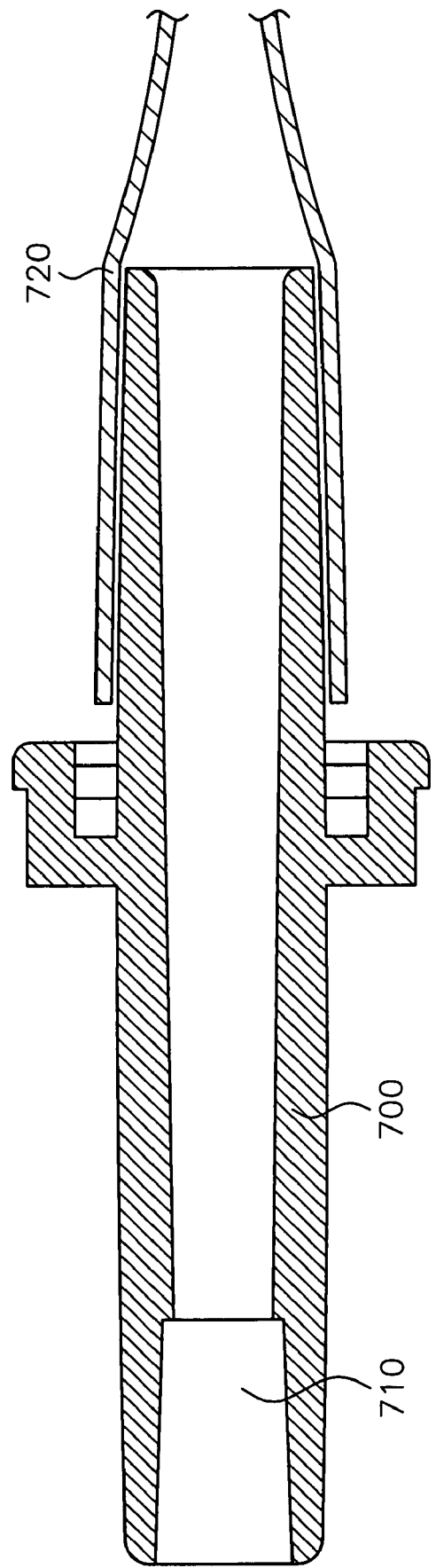
FIG. 7 shows a cross-sectional view of a male blunt cannula used in accordance with the present invention.

A preferred connection between the product bag fill line and outlet tube connector 300 is a blunt cannula connector. In accordance with the present invention, an exemplary blunt cannula is shown in FIG. 7. FIG. 7 shows a blunt male cannula 700 having a female port 710 on at least one end. FIG. 7 shows blunt male cannula 700 disposed on the end of product bag fill line 720. The end having female port 710 is the end which would be thrust into the septum in order to establish fluid flow as described above. The advantage to having a female port disposed within a male cannula is seen when one realizes how these TPN bags are typically used.

Often, after a TPN product bag has been filed in accordance with the above, it may be desirable to take additional steps. These additional steps would include possibly adding a very small amount of some additional ingredient, or withdrawing a small sample of the product composition. Often such an addition or sampling requires the addition or withdrawal of a small amount of fluid, such as 1 to 5 cc of fluid. The female port on male blunt cannula 700 as described above allows for the insertion of a standard syringe and subsequent sealing of that syringe against the female port wall to form a seal and allow the withdrawal or addition of a small amount of fluid. Moreover, after the product bag has been filled, the male blunt cannula can be withdrawn from the septum of the outlet tube connector 300. Then, a syringe can be inserted and lodged within female port 710 of male blunt cannula 700 to allow for the syringe to act on the fluid within the product bag.

Figure 8:
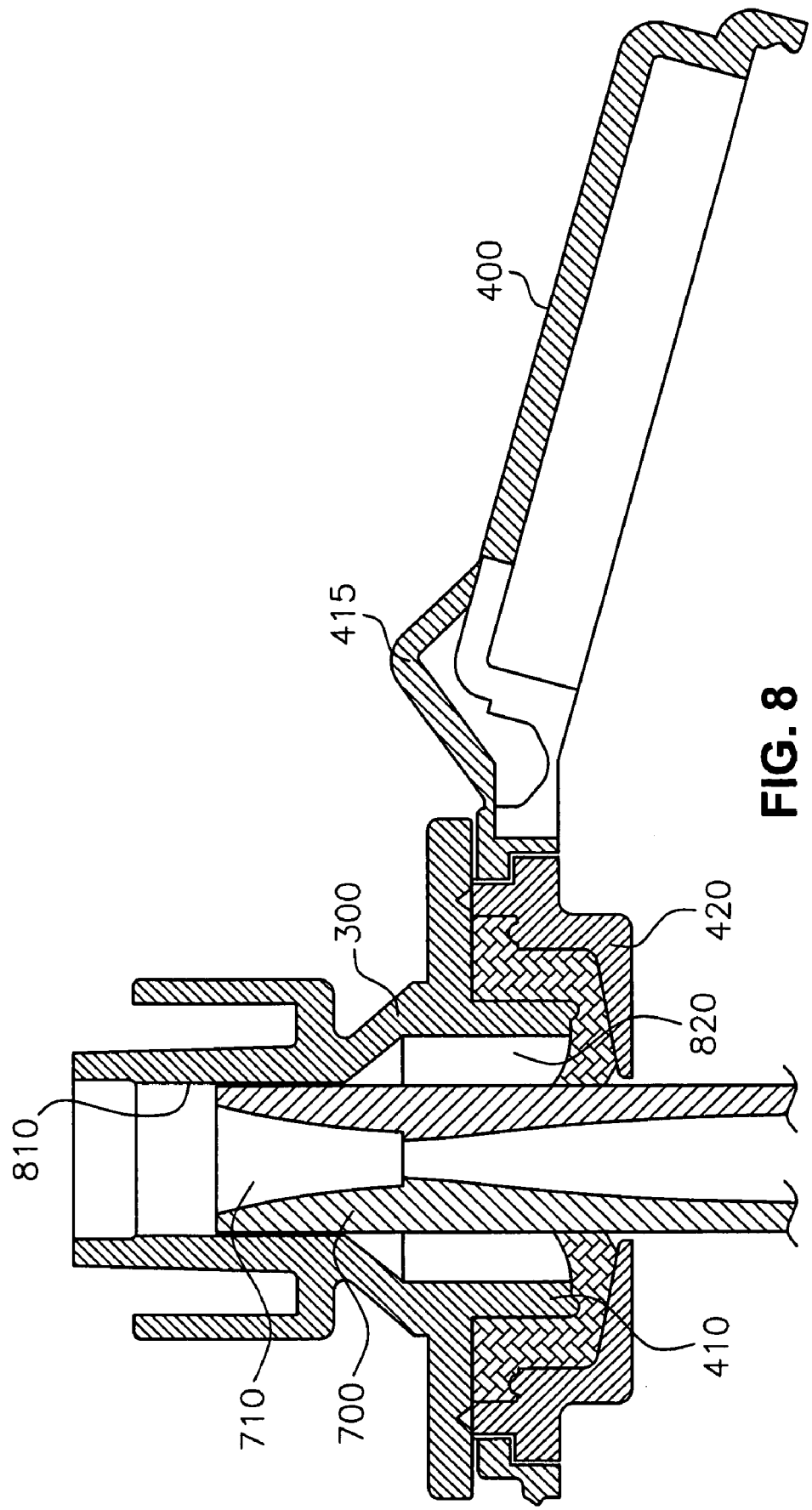
FIG. 8 shows the male blunt cannula of FIG. 7 inserted into an outlet tube connector in accordance with the present invention.

Another aspect of the male blunt cannula is that it can be inserted through septum 440 and lodged within outlet tube connector 300 along the inside wall of outlet tube connector 300. FIG. 8 shows such a friction fit between male blunt cannula 700 and inner wall 810 of outlet tube connector 300. Such a fit is encouraged by the slightly decreasing inside diameter of outlet tube connector 300 as one moves from its distal end toward manifold outlet port 310. Such a slightly conical inner surface aids in the friction fit. An additional advantage of this configuration is that it further reduces the common volume of the manifold because the area outside the cannula wall, but inside outlet tube connector 300, shown in FIG. 8 as space 820, is removed from the flow volume.

It is noteworthy, also, that when the cannula is withdrawn from the manifold outlet tube connector 300, a vacuum is momentarily created within the manifold as the cannula is pulled out and the septum prevents air from filling the volume until the cannula is completely out of the outlet tube connector and the pressure within the system is allowed to stabilize. This vacuum can pull additional fluid which is residing in any (or all) of the feed tubes into the manifold. Such a pulling of fluid is, of course, undesirable, especially in the case of the lipid line for the reasons discussed above. In order to prevent such a pulling of fluid, the check-valves should be designed such that they do not break at the negative pressure created when the vacuum is made upon cannula withdrawal. This is especially important for the lipid line check-valve which, as discussed above, in the preferred embodiment is in the port closest to the outlet port. Thus, it is a feature of the present invention that the cracking pressure of the check valves (the pressure at which the check valve opens, or releases) exceed the absolute value of the vacuum pressure created upon cannula withdrawal. In one embodiment of the invention, the cracking pressure of at least the check valve disposed in the lipid line (for example check-valve disk 150 in center port 140) exceeds the absolute value of the vacuum pressure created upon cannula withdrawal.

Figure 9:
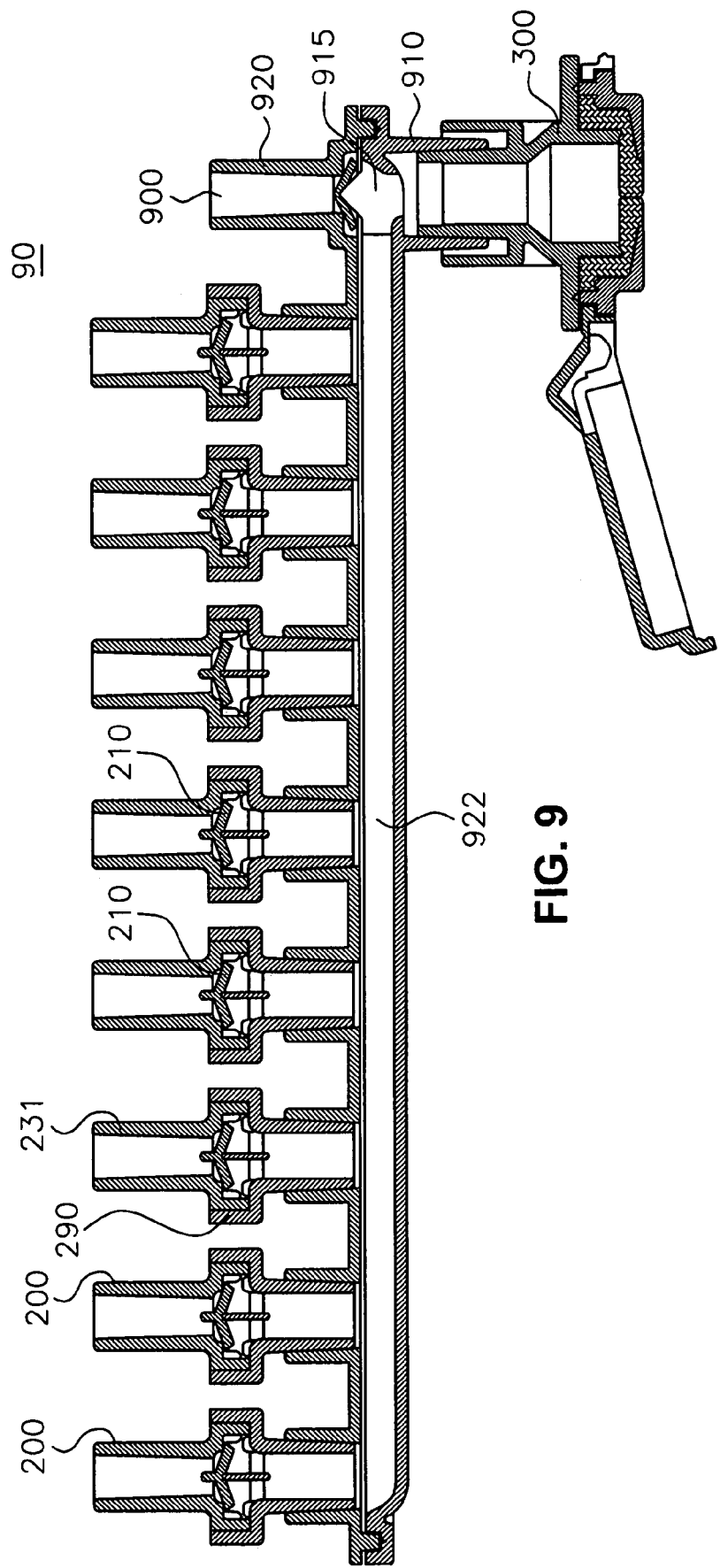
FIG. 9 shows a cross-sectional view of a linear manifold embodiment in accordance with the present invention.

Although round manifolds have been discussed and illustrated thus far, it is a part of the present invention that other shapes of manifolds can be used. FIG. 9 shows a view of such an alternatively shaped manifold, namely a linear manifold 90 having coaxial inlet 900 (for the lipid line) defined by coaxial inlet port 920 being coaxial with outlet port 910. As noted above, such a configuration minimizes the volume in which lipid solutions can accumulate. Essentially all other parts, such as valve housings 200 and check-valve disks 210, are the same as those disclosed above with respect to the round manifold configuration. The primary difference between this embodiment and those disclosed above with respect to the round manifold configuration is that no gasket is used in this embodiment and a single common flow channel 922 connects all inlets (except coaxial inlet 900) to common central chamber 915.

Figure 10A:
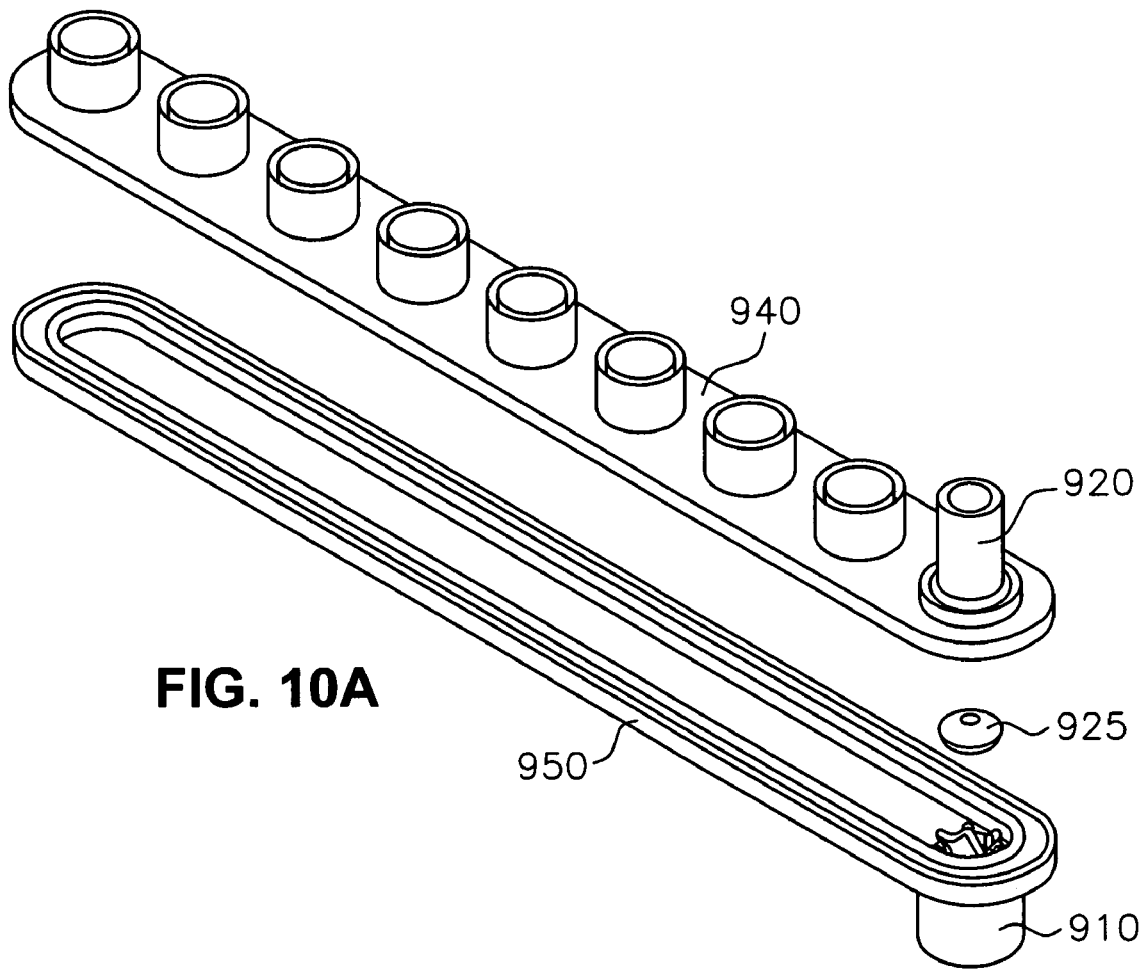
FIG. 10a is an exploded view of the linear manifold shown in FIG. 9.
Figure 10B:
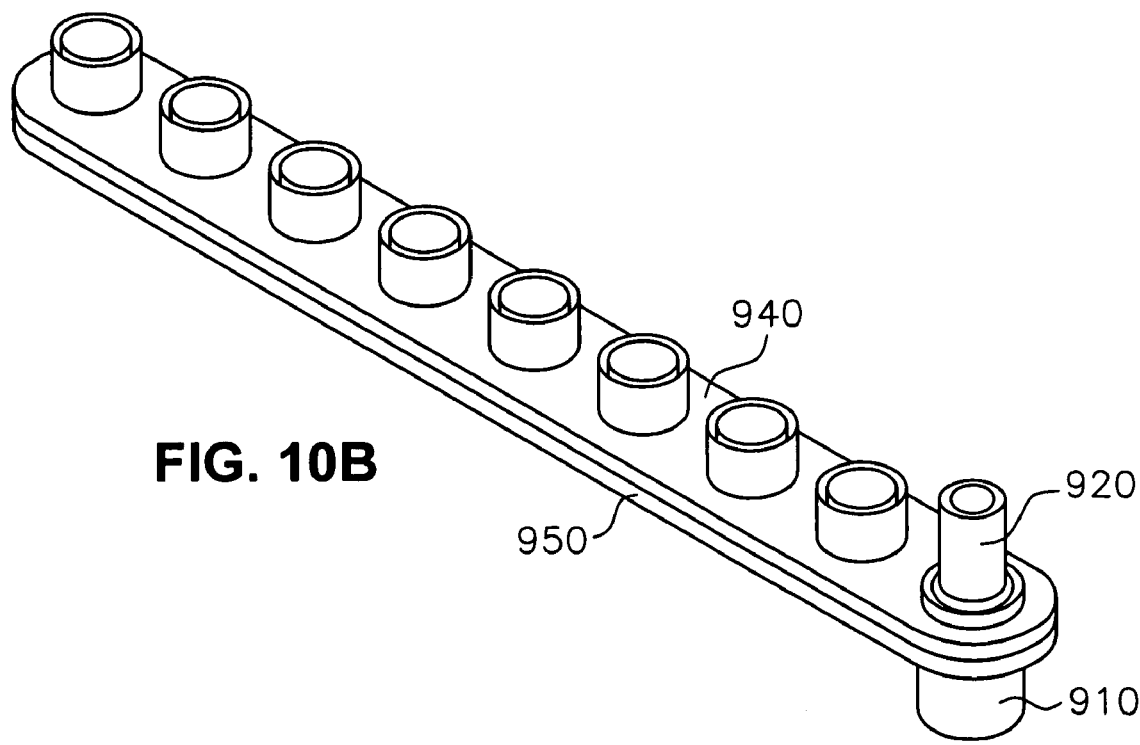

FIG. 10a shows an exploded view of manifold 90 (without any valve housings or outlet tube connector 300), with manifold top 940 shown disposed above manifold bottom 950 and check-valve disk 925 of coaxial inlet port 920 shown disposed therebetween. FIG. 10b shows these components of manifold 90 assembled. Of course, as above, any number of inlets could be provided. FIGS. 10a and 10b illustrate a preferred embodiment having 9 total inlets, including coaxial inlet port 920.

Included as a part of the present invention is a method of minimizing error in the filling of a product bag in a bulk compounding system. The method comprises the steps of providing a manifold with a minimum common volume to minimize residual holding of any one ingredient solution, and passing individual ingredient solutions through the manifold to fill a product bag. Error is reduced because of the minimization of the manifold common volume step.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A manifold for receiving fluid tubes in a bulk compounder, said manifold comprising:
   a plurality of valve housings each defined by an upper portion, a lower portion, and a check-valve disposed between said upper portion and said lower portion;
   a common flow channel in fluid communication with said lower portion of each said plurality of valve housings;
   an outlet in fluid communication with said common flow channel; and
   an inlet port which is coaxial with said outlet, said coaxial inlet port containing a check-valve.

2. The manifold of claim 1 further comprising a central chamber in fluid communication with each said plurality of valve housings for fluidly connecting said plurality of valve housings to said outlet.

3. The manifold of claim 1 wherein said outlet comprises an outlet port having a self-sealing membrane adapted to be penetrated by a cannula.

4. The manifold of claim 1 wherein said outlet comprises an outlet port having a self-sealing membrane adapted to be penetrated by a cannula, and
   wherein said coaxial inlet port check-valve is adapted to have a cracking pressure greater than the vacuum pressure within said outlet port when the cannula is pulled from said self-sealing membrane.

5. The manifold of claim 4 wherein all said check-valves are adapted to have a cracking pressure greater than the vacuum pressure within said outlet port when the cannula is pulled from said self-sealing membrane.

6. The manifold of claim 1 wherein said plurality of valve housings are disposed linearly with respect to each other.

7. A manifold set for receiving fluid tubes in a bulk compounder comprising:
   a manifold, said manifold comprising:
   a plurality of valve housings each defined by an upper portion, a lower portion, and a check-valve disposed between said upper portion and said lower portion;
   a common flow channel in fluid communication with said lower portion of each said plurality of valve housings;
   an outlet having a self-sealing membrane, said outlet in fluid communication with said common flow channel; and
   an inlet port which is coaxial with said outlet, said coaxial inlet port containing a check-valve; and
   a cannula having at least one male blunt tip for insertion into said self-sealing membrane.

8. The manifold set of claim 7 wherein said cannula has a female port at said male blunt tip end for receiving an additional male tip.

9. A tube set for use in bulk compounding, said tube set comprising:
   a plurality of pump sections, each said pump section having a distal end;
   a plurality of tubes, each said tube of said plurality having a distal end and proximal end, each said proximal end of each tube of said plurality attached to said distal end of a respective pump section, and each said distal end of each tube of said plurality attached to a manifold, said manifold comprising:
   a plurality of valve housings each defined by an upper portion, a lower portion, and a check-valve disposed between said upper portion and said lower portion;
   a common flow channel in fluid communication with said lower portion of each said plurality of valve housings;
   an outlet in fluid communication with said common flow channel; and
   an inlet port which is coaxial with said outlet, said coaxial inlet port containing a check-valve.

10. The tube set of claim 9 wherein said plurality of valve housings is six.

11. The tube set of claim 9 wherein said plurality of valve housings is nine.

12. A tube set for use in bulk compounding, said tube set comprising:
   a plurality of pump sections, each said pump section having a distal end and a proximal end;
   a first plurality of tubes, each said tube of said first plurality attached to said proximal end of a respective pump section;
   a second plurality of tubes, each said tube of said second plurality having a distal end and proximal end, each said proximal end of each tube of said second plurality attached to said distal end of a respective pump section, and said distal end of each tube of said second plurality attached to a manifold, said manifold comprising:
   a plurality of valve housings each defined by an upper portion, a lower portion, and a check-valve disposed between said upper portion and said lower portion;
   a common flow channel in fluid communication with lower portion of each said plurality of valve housings;
   an outlet in fluid communication with said common flow channel; and
   an inlet port which is coaxial with said outlet, said coaxial inlet port containing a check-valve.

13. The tube set of claim 12 wherein said first and second plurality are both six.

14. The tube set of claim 12 wherein said first and second plurality are both nine.

* * * * *